United States Patent
Yu

(10) Patent No.: US 12,111,280 B2
(45) Date of Patent: Oct. 8, 2024

(54) BIOSENSING SYSTEMS HAVING BIOSENSORS COATED WITH CO-POLYMERS AND USES THEREOF

(71) Applicant: MICROTECH MEDICAL (HANGZHOU) CO., LTD., Hangzhou (CN)

(72) Inventor: Fei Yu, Hangzhou (CN)

(73) Assignee: MICROTECH MEDICAL (HANGZHOU) CO., LTD., Hangzhou (CN)

(*) Notice: Subject to any disclaimer, the term of this patent is extended or adjusted under 35 U.S.C. 154(b) by 1275 days.

(21) Appl. No.: 16/638,870

(22) PCT Filed: Apr. 30, 2019

(86) PCT No.: PCT/CN2019/085200
§ 371 (c)(1),
(2) Date: Feb. 13, 2020

(87) PCT Pub. No.: WO2020/220263
PCT Pub. Date: Nov. 5, 2020

(65) Prior Publication Data
US 2021/0255133 A1    Aug. 19, 2021

(51) Int. Cl.
*G01N 27/327* (2006.01)
*C08G 18/40* (2006.01)
(Continued)

(52) U.S. Cl.
CPC ....... *G01N 27/3272* (2013.01); *G01N 33/487* (2013.01)

(58) Field of Classification Search
CPC .. G01N 27/327; G01N 27/3272; G01N 27/40; G01N 27/3278; G01N 33/49;
(Continued)

(56) References Cited

U.S. PATENT DOCUMENTS

2004/0154933 A1    8/2004   Cosofret

FOREIGN PATENT DOCUMENTS

| CN | 106290520 A | 1/2017 |
| CN | 106397727 A | 2/2017 |
| CN | 106290530 B | 10/2018 |

OTHER PUBLICATIONS

CN 106290530A—English machine Translation (Year: 2016).*
CN106290520—English machine Translation (Year: 2016).*
CN106397727—English machine Translation (Year: 2016).*

* cited by examiner

*Primary Examiner* — Gurpreet Kaur
(74) *Attorney, Agent, or Firm* — Bayramoglu Law Offices LLC

(57) ABSTRACT

A biosensing system having biosensors coated with co-polymers and their uses thereof includes a substrate, a working electrode on top of the substrate, a detection layer on top of the working electrode, a biocompatible membrane on top of the detection layer, a blank electrode, wherein the blank electrode is substantially same as the working electrode and covered directly by the biocompatible membrane, a reference electrode, and a counter electrode; a DC power supply; a current measuring unit; an AC impedance measuring unit; a circuit switch; a control unit; and a data processing unit, wherein the peptide probe includes an enzyme, an antibody, or a polymer comprising a peptide, wherein the peptide probe includes an oxidoreductase, wherein the peptide probe includes glucose oxidase, glucose dehydrogenase, or horseradish peroxidase, wherein the metallic nanoparticle is a platinum nanoparticle, a gold nanoparticle, or an iridium nanoparticle.

32 Claims, 8 Drawing Sheets

(51) Int. Cl.
*C08G 18/44* (2006.01)
*C08G 18/50* (2006.01)
*C08G 18/61* (2006.01)
*C08G 18/62* (2006.01)
*G01N 27/30* (2006.01)
*G01N 33/487* (2006.01)

(58) Field of Classification Search
CPC .. G01N 33/80; G01N 33/26; G01N 33/48707; G01N 33/487
See application file for complete search history.

BIOSENSING SYSTEMS HAVING BIOSENSORS COATED WITH CO-POLYMERS AND USES THEREOF

CROSS REFERENCE TO THE RELATED APPLICATIONS

This application is the national phase entry of the International Application No. PCT/CN2019/085200, filed on Apr. 30, 2019, the entire contents of which are incorporated herein by reference.

TECHNICAL FIELD

The present invention relates to biosensing systems having biosensors coated with co-polymers and their uses thereof.

BACKGROUND

Electrochemical biosensors that employ biological recognition systems and electrochemical transudation offer a possibility of quick and real-time analysis, which is particularly suited for the rapid measurement of point-of-care industry. The outer membrane of a biosensor is very important, as it represents the interface between the sensor and the analyte medium. The purpose of this interface membrane is to allow the diffusion of analytes into the detection layer while excluding potential interfering species which may be present in the analyte medium. Because an interface membrane may be less effective in excluding interfering species whose size is similar to that of the analyte, there is a need for biosensing systems with improved properties of eliminating interfering signals.

SUMMARY

In one aspect, provided is a biosensing system, comprising:
(1) a biosensor, comprising:
  a substrate,
  a working electrode on top of the substrate,
  a detection layer on top of the working electrode,
  a biocompatible membrane on top of the detection layer,
  a blank electrode, wherein the blank electrode is substantially same as the working electrode and covered directly by the biocompatible membrane,
  a reference electrode, and
  a counter electrode;
(2) a DC power supply;
(3) a current measuring unit;
(4) an AC impedance measuring unit;
(5) a circuit switch;
(6) a control unit; and
(7) a data processing unit.

In some embodiments according to the embodiment above, the working electrode comprises carbon, graphene, gold, or platinum.

In some embodiments according to any of the embodiments above, the detection layer comprises a metallic nanoparticle, polydopamine, and a peptide probe.

In some embodiments according to any of the embodiments above, the metallic nanoparticle is a platinum nanoparticle, a gold nanoparticle, or an iridium nanoparticle.

In some embodiments according to any of the embodiments above, the metallic nanoparticle has a dimension of between about 1 and about 100 nanometers.

In some embodiments according to any of the embodiments above, the peptide probe comprises an enzyme, an antibody, or a polymer comprising a peptide.

In some embodiments according to any of the embodiments above, the peptide probe comprises an oxidoreductase.

In some embodiments according to any of the embodiments above, the peptide probe comprises glucose oxidase, glucose dehydrogenase, or horseradish peroxidase.

In some embodiments according to any of the embodiments above, the metallic nanoparticle is coated with polydopamine and the peptide probe. In some embodiments according to any of the embodiments above, the metallic nanoparticle is admixed with polydopamine and the peptide probe.

In some embodiments according to any of the embodiments above, the biocompatible membrane comprises a triblock polymer A-b-B-b-C, wherein: A is a hydrophilic soft segment, B is a hydrophobic hard segment, C is a flexible polymer segment, and b is a chain extender.

In some embodiments according to any of the embodiments above, the hydrophilic soft segment comprises a polymer selected from the group consisting of polyethylene glycol (PEG), polypropylene glycol (PPG), and polyetheramine (PEA).

In some embodiments according to any of the embodiments above, the hydrophobic hard segment comprises a polymer selected from the group consisting of polycarbonate (PC) and poly(methyl methacrylate) (PMMA).

In some embodiments according to any of the embodiments above, the flexible polymer segment comprises a polymer selected from the group consisting of polydimethylsiloxane (PDMS) and poly(2-hydroxyethyl methacrylate) (PHEMA).

In some embodiments according to any of the embodiments above, the chain extender in the biocompatible membrane is derived from a compound comprising an isocyanate.

In some embodiments according to any of the embodiments above, each chain extender is independently derived from methylene diphenyl diisocyanate (MDI), hexamethylene diisocyanate (HDI), or bis(4-isocyanatocyclohexyl)methane.

In some embodiments according to any of the embodiments above, the number average molecular weight of A is between about 200 and about 10000, the number average molecular weight of B is between about 1000 and about 20000, and the number average molecular weight of C is between about 1000 and about 20000.

In some embodiments according to any of the embodiments above, the biocompatible membrane comprises: between about 1 and about 10 parts by weight of A, between about 1 and about 5 parts by weight of B, between about 1 and about 5 parts by weight of C, and between about 1 and about 3 parts by weight of b.

In some embodiments according to any of the embodiments above, the linkage between each of A-b, B-b, and C-b is independently a urea linkage or a carbamate linkage.

In some embodiments according to any of the embodiments above, the biosensor further comprises an adhesive layer between the detection layer and the biocompatible membrane on top of the working electrode and between the biocompatible membrane and the blank electrode, wherein the adhesive layer comprises a polymer comprising a first monomer comprising at least two amine moieties crosslinked with a second monomer comprising at least two formyl moieties.

In some embodiments according to any of the embodiments above, the first monomer is 1,6-diaminohexane and the second monomer is glutaraldehyde.

In some embodiments according to any of the embodiments above, the minimum distance between the working electrode and the blank electrode is no more than about 5 mm.

In some embodiments according to any of the embodiments above, the DC power supply comprises: a first circuit configured to apply a DC voltage to the working electrode, thereby generating a direct current on top of the working electrode; and a second circuit configured to apply a DC voltage to the blank electrode, thereby generating a direct current on the blank electrode, wherein the first circuit and second circuit are connected in parallel and the DC voltage applied to the working electrode and the DC voltage applied to the blank electrode are same relative to the reference electrode.

In some embodiments according to any of the embodiments above, the current measuring unit comprises: a first current measuring device configured to measure the direct current on the working electrode and communicate data regarding the direct current on the working electrode to the data processing unit, and a second current measuring device configured to measure the direct current on the working electrode and communicate data regarding the direct current on the blank electrode to the data processing unit.

In some embodiments according to any of the embodiments above, the AC impedance measuring unit is configured to apply a voltage comprising a DC component and an AC component to the working electrode and blank electrode, to measure a resulting current on the working electrode and a resulting current on the blank electrode, to determine an AC impedance of the working electrode and an AC impedance of the blank electrode, and to communicate data regarding the resulting currents and the AC impedances to the data processing unit.

In some embodiments according to any of the embodiments above, AC component has a frequency of about 1-100 kHz.

In some embodiments according to any of the embodiments above, the data from the AC impedance measuring unit comprises the magnitude, phase, real part, and/or imaginary part of the measured AC impedance.

In some embodiments according to any of the embodiments above, the operation frequency of the current measuring unit is at least about 10 times of the operation frequency of the AC impedance measuring unit.

In another aspect, provided is a method of using the biosensing system of any of the embodiments above, comprising: (1) applying a DC voltage to the working electrode and the blank electrode, thereby generating a direct current on the working electrode and a direct current on the blank electrode; (2) measuring the direct current on the working electrode and the direct current on the blank electrode; (3) measuring an AC impedance of the working electrode and/or an AC impedance of the blank electrode; and (4) determining concentration of the analyte based on the measured direct currents and AC impedances.

In some embodiments of using the biosensing system according to any of the embodiments above, step (1) comprises: (a) applying a DC voltage to the working electrode, thereby generating a direct current on the working electrode; and (b) applying a DC voltage to the blank electrode, thereby generating a direct current on the blank electrode, wherein the DC voltage applied to the working electrode and the DC voltage applied to the blank electrode are same relative to the reference electrode.

In some embodiments of using the biosensing system according to any of the embodiments above, step (3) comprises: (a) applying a voltage comprising a DC component and an AC component to the working electrode and blank electrode; (b) measuring a resulting current on the working electrode and a resulting current on the blank electrode; and (c) determining an AC impedance of the working electrode and an AC impedance of the blank electrode.

In some embodiments of using the biosensing system according to any of the embodiments above, step (4) comprises:
(a) reading a direct current (I1) on the working electrode, the time (t1) when I1 is measured, a direct current (I2) on the blank electrode, the time (t2) when I2 is measured, wherein t2 is within ±30 seconds from t1;
(b) determining an analyte current (I) and a time (t) using the following formulae:

$$I = I1 - I2, \text{ and} \qquad (i)$$

$$t = (t1 \pm t2)/2; \qquad (ii)$$

(c) determining concentration of the analyte (C1) using the formula $C1 = f(I, X)$, wherein $f(I, X) = (I-b)*X$, b is a pre-determined background current value, X is a conversion factor determined using the following steps:
(i) determining if the biosensor has been calibrated,
in response to the determination that the biosensor has not been calibrated, setting X' as a predetermined value X0 and setting the calibration time as 0, and
in response to the determination that biosensor has been calibrated, determining X' using the formula $X' = f^{-1}(I(tc0), C0)$ and setting tc' as tc0, wherein $f^{-1}(I(tc0), C0)$ is inverse operation of $f(I, X)$, C0 is the concentration of the analyte in the calibration, tc0 is the time when the calibration is conducted, I(tc0) is an analyte current measured at a time closest to the latest calibration, wherein I(tc0) is measured within 5 minutes before or after the latest calibration,
(ii) determining if the latest calibration time is after the latest measurement of impedance,
in response to the determination that the latest calibration time is after the latest impedance measurement, setting X as X' and finishing the determination of X,
in response to the determination that the latest calibration time is not after the latest impedance measurement, reading the real part of the latest impedance (Zre_cal) and the imaginary part of the latest impedance (Zim_cal) and proceeding to step (iii),
(iii) determining if the real part of the currently measured impedance (Zre) is within a first predetermined range and if the imaginary part of the currently measured impedance (Zim) is within a second predetermined range,
in response to the determination that Zre is not within the first predetermined range or Zim is not within the second predetermined range, sending an error message and finishing the determination of X, in response to the determination that Zre is within the first predetermined range and Zim is within the second predetermined range, proceeding to step (iv), (iv) determining the real part difference (dZre) and the imaginary part difference (dZim) using the following formulae:

$dZre=Zre-Zre\_cal$, and $dZim=Zim-Zim\_cal$, (v) determining if absolute value of dZre is larger than a predetermined threshold dZre_thres and if absolute value of dZim is larger than a predetermined threshold dZim_thres, in response to the determination that absolute value of dZre is not larger than dZre_thres and absolute value of dZim is not larger than dZim_thres, setting X as X' and finishing the determination of X, in response to the determination that absolute value of dZre is larger than dZre_thres or absolute value of dZim is larger than dZim_thres, proceeding to steps (vi)-(x), (vi) in response to the determination that dZre>0, dZre>dZre_thres, dZim>0, and dZim>dZim_thres, setting X=X'*h(Zre/Zre_cal, Zim/Zim_cal), wherein h(Zre/Zre_cal, Zim/Zim_cal)>1, (vii) in response to the determination that dZre>0, dZre>dZre_thres, and dZim≤dZim_thres, setting X=X'*j(Zre/Zre_cal), wherein j(Zre/Zre_cal)>1, (viii) in response to the determination that dZre<0 and dZre←dZre_thres, setting X=X'*k(Zre/Zre_cal), wherein k(Zre/Zre_cal)<1, (ix) in response to the determination that −dZre_thres<dZre<dZre_thres, dZim>0, and dZim>dZim_thres, setting X=X'*m(Zim/Zim_cal), wherein m(Zim/Zim_cal)>1, (x) in response to the determination that −dZre_thres<dZre<dZre_thres, dZim<0, and dZim←dZim_thres, setting X=X'*n(Zim/Zim_cal), wherein n(Zim/Zim_cal)<1.

In some embodiments of using the biosensing system according to any of the embodiments above, the method further comprises a step of determining the condition of the biosensor, wherein the step is conducted within 5 minutes after the biosensor is coupled to the DC power supply, current measuring unit, AC impedance measuring unit, circuit switch control unit, and data processing unit and comprises:

(a) measuring an AC impedance of the working electrode;
(b) determining if the real part of the measured impedance (Zre) is within a first predetermined range and if the imaginary part of the currently measured impedance (Zim) is within a second predetermined range, in response to the determination that Zre is not within the first predetermined range or Zim is not within the second predetermined range, starting an initialization sequence to prepare the biosensor, in response to the determination that Zre is within the first predetermined range and Zim is within the second predetermined range, proceeding to step (1).

DETAILED DESCRIPTION OF THE EMBODIMENTS

Definitions

Figure 1:
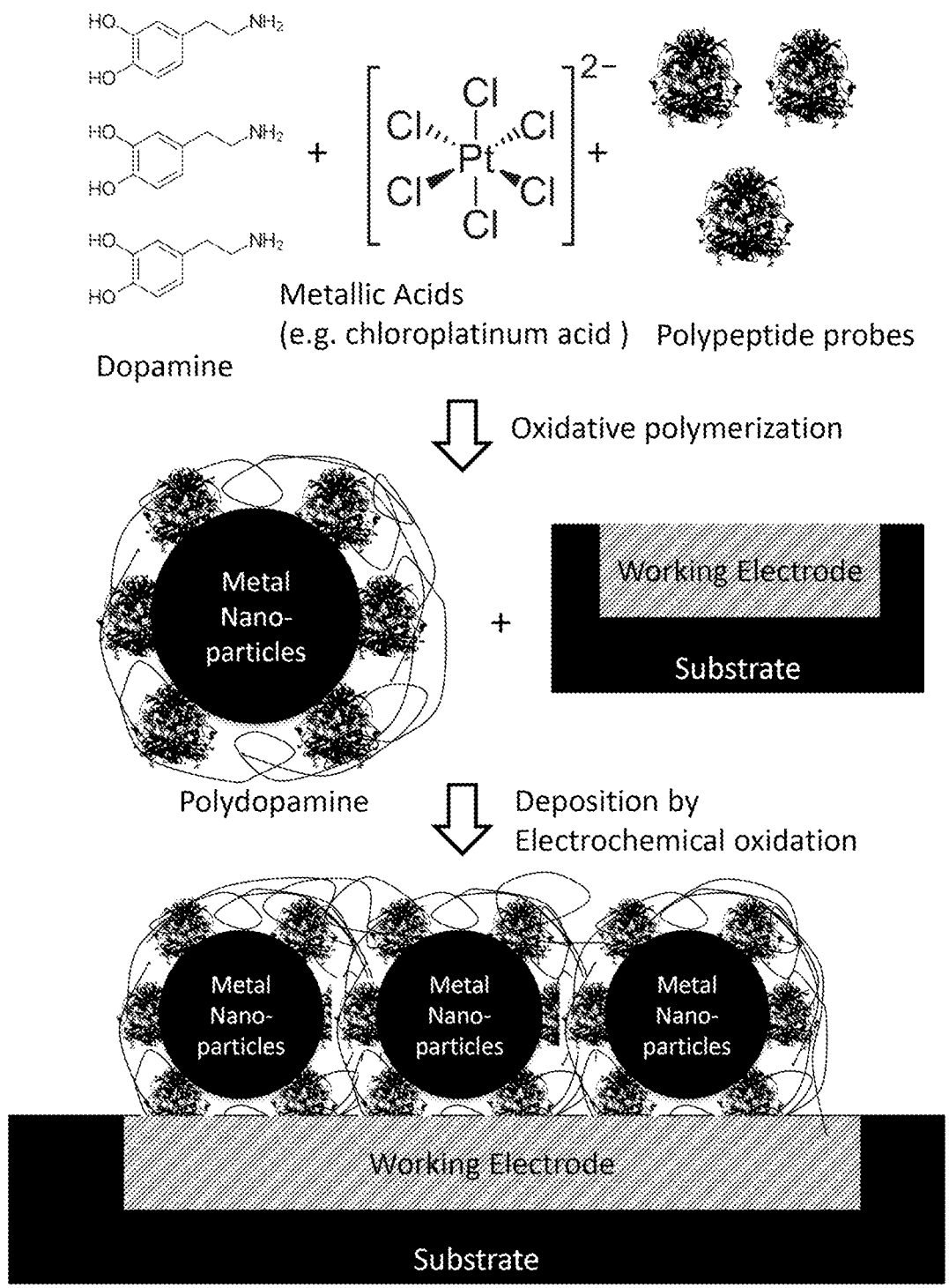
FIG. 1 shows an exemplary process of forming the detection layer on top of the working electrode.

Unless defined otherwise, all technical and scientific terms used herein have the same meaning as is commonly understood by one of ordinary skill in the art to which this invention belongs. All patents, applications, published applications, other publications and databases referred to herein are incorporated by reference in their entirety. If a definition set forth in this section is contrary to or otherwise inconsistent with a definition set forth in applications, published applications and other publications that are herein incorporated by reference, the definition set forth in this section prevails over the definition that is incorporated herein by reference.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

As used herein, "a" or "an" means "at least one" or "one or more."

As used herein, the terms "including," "containing," and "comprising" are used in their open, non-limiting sense.

For clarity of disclosure, and not by way of limitation, the detailed description of the invention is divided into the subsections that follow.

Biosensing System

In one aspect, provided is a biosensing system, comprising:

(1) a biosensor, comprising:
   a substrate,
   a working electrode on top of the substrate,
   a detection layer on top of the working electrode,
   a biocompatible membrane on top of the detection layer,
   a blank electrode, wherein the blank electrode is substantially same as the working electrode and covered directly by the biocompatible membrane,
   a reference electrode, and
   a counter electrode;
(2) a DC power supply;
(3) a current measuring unit;

(4) an AC impedance measuring unit;
(5) a circuit switch;
(6) a control unit; and
(7) a data processing unit.

Examples of substrate materials include, but are not limited to, inorganic materials such as glass and silicon wafer, and organic materials such as polyimide and polydimethylsiloxane. In some embodiments, the substrate comprises glass. In some embodiments, the substrate comprises silicon wafer. In some embodiments, the substrate comprises polyimide. In some embodiments, the substrate comprises polydimethylsiloxane.

In some embodiments, the working electrode may be prepared using any suitable conductive materials. In some embodiments, the working electrode comprises carbon, graphene, gold, or platinum. In some embodiments, the working electrode comprises carbon. In some embodiments, the working electrode comprises graphene. In some embodiments, the working electrode comprises gold. In some embodiments, the working electrode comprises platinum.

In some embodiments, the detection layer comprises a metallic nanoparticle, polydopamine, and a peptide probe. In some embodiments, the term "nanoparticle" refers to a nanoscale particle with a size that is measured in nanometers. In some embodiments, the metallic nanoparticle is a platinum nanoparticle, a gold nanoparticle, or an iridium nanoparticle. In some embodiments, the metallic nanoparticle is a platinum nanoparticle. In some embodiments, the metallic nanoparticle is a gold nanoparticle. In some embodiments, the metallic nanoparticle is an iridium nanoparticle.

In some embodiments, the metallic nanoparticle has a dimension of between about 1 and about 900, between about 1 and about 800, between about 1 and about 700, between about 1 and about 600, between about 1 and about 500, between about 1 and about 400, between about 1 and about 300, between about 1 and about 200, between about 1 and about 100, between about 1 and about 50, between about 50 and about 900, between about 50 and about 800, between about 50 and about 700, between about 50 and about 600, between about 50 and about 500, between about 50 and about 400, between about 50 and about 300, between about 50 and about 200, between about 50 and about 100, between about 100 and about 900, between about 200 and about 800, between about 200 and about 700, between about 200 and about 600, between about 200 and about 500, between about 200 and about 400, between about 200 and about 300, 300 and about 900, between about 300 and about 800, between about 300 and about 700, between about 300 and about 600, between about 300 and about 500, between about 300 and about 400, 400 and about 900, between about 400 and about 800, between about 400 and about 700, between about 400 and about 600, between about 400 and about 500, between about 500 and about 900, between about 500 and about 800, between about 500 and about 700, between about 500 and about 600, between about 600 and about 900, between about 600 and about 800, between about 600 and about 700, between about 700 and about 900, between about 700 and about 800, between about 800 and about 900, between about 1 and about 90, between about 1 and about 80, between about 1 and about 70, between about 1 and about 60, between about 1 and about 50, between about 1 and about 40, between about 1 and about 30, between about 1 and about 20, or between about 1 and about 10 nanometers. In some embodiments, the metallic nanoparticle has a dimension of less than about 900, about 800, about 700, about 600, about 500, about 400, about 300, about 200, about 100, about 90, about 80, about 70, about 60, about 50, about 40, about 30, about 20, or about 10 nanometers. In some embodiments, the metallic nanoparticle has a dimension of at least about 900, about 800, about 700, about 600, about 500, about 400, about 300, about 200, about 100, about 90, about 80, about 70, about 60, about 50, about 40, about 30, about 20, or about 10 nanometers. In some embodiments, the metallic nanoparticle has a dimension of about 900, about 800, about 700, about 600, about 500, about 400, about 300, about 200, about 100, about 90, about 80, about 70, about 60, about 50, about 40, about 30, about 20, or about 10 nanometers. In some embodiments, the metallic nanoparticle has a dimension of between about 1 and about 100 nanometers.

In some embodiments, the peptide probe comprises an enzyme, an antibody, or a polymer comprising a peptide. In some embodiments, the peptide probe comprises an enzyme. In some embodiments, the peptide probe comprises an oxidoreductase. In some embodiments, the peptide probe comprises an oxidase such as glucose oxidase, glutamate oxidase, alcohol oxidase, lactate oxidase, ascorbate oxidase, cholesterol oxidase, or choline oxidase. In some embodiments, the peptide probe comprises a dehydrogenase such as alcohol dehydrogenase, glutamate dehydrogenase, glucose dehydrogenase, or lactate dehydrogenase. In some embodiments, the peptide probe comprises a peroxidase such as horseradish peroxidase. In some embodiments, the peptide probe comprises glucose oxidase, glutamate oxidase, alcohol oxidase, lactate oxidase, ascorbate oxidase, cholesterol oxidase, choline oxidase, alcohol dehydrogenase, glutamate dehydrogenase, glucose dehydrogenase, lactate dehydrogenase, or horseradish peroxidase. In some embodiments, the peptide probe comprises glucose oxidase, glucose dehydrogenase, or horseradish peroxidase. In some embodiments, the peptide probe comprises an antibody such as hepatitis B antibody. In some embodiments, the peptide probe comprises a polymer comprising a peptide.

In some embodiments, the metallic nanoparticle is coated with polydopamine and the peptide probe. In some embodiments, the metallic nanoparticle is admixed with polydopamine and the peptide probe.

In some embodiments, the biocompatible membrane comprises a triblock polymer A-b-B-b-C, wherein A is a hydrophilic soft segment. In some embodiments, the hydrophilic soft segment comprises a polymer selected from the group consisting of polyethylene glycol (PEG), polypropylene glycol (PPG), and polyetheramine (PEA). In some embodiments, the hydrophilic soft segment comprises PEG. In some embodiments, the hydrophilic soft segment comprises PPG. In some embodiments, the hydrophilic soft segment comprises PEA. In some embodiments, the hydrophilic soft segment comprises at least two polymers selected from the group consisting of PEG, PPG, and PEA. In some embodiments, the hydrophilic soft segment comprises PEG, PPG, and PEA.

In some embodiments, the biocompatible membrane comprises a triblock polymer A-b-B-b-C, wherein B is a hydrophobic hard segment. In some embodiments, the hydrophobic hard segment comprises a polymer selected from the group consisting of polycarbonate (PC) and poly(methyl methacrylate) (PMMA). In some embodiments, the hydrophobic hard segment comprises PC. In some embodiments, the hydrophobic hard segment comprises PMMA. In some embodiments, the hydrophobic hard segment comprises PC and PMMA.

In some embodiments, the biocompatible membrane comprises a triblock polymer A-b-B-b-C, wherein C is a flexible polymer segment. In some embodiments, the flexible polymer segment comprises a polymer selected from the group consisting of polydimethylsiloxane (PDMS) and poly(2-hydroxyethyl methacrylate) (PHEMA). In some embodiments, the flexible polymer segment comprises PDMS. In some embodiments, the flexible polymer segment comprises PHEMA. In some embodiments, the flexible polymer segment comprises PDMS and PHEMA.

In some embodiments, the biocompatible membrane comprises a triblock polymer A-b-B-b-C, wherein b is a chain extender. In some embodiments, the chain extender in the biocompatible membrane is derived from a compound comprising an isocyanate (i.e., a —NCO group). In some embodiments wherein each chain extender is independently derived from methylene diphenyl diisocyanate (MDI), hexamethylene diisocyanate (HDI), or bis(4-isocyanatocyclohexyl)methane. In some embodiments, the chain extender is MDI. In some embodiments, the chain extender is HDI. In some embodiments, the chain extender is bis(4-isocyanatocyclohexyl)methane.

In some embodiments, the molecular weight of each of A, B, and C is determined by measuring he molecular mass of n polymer molecules, summing the masses, and dividing the total mass by n (i.e., number average molecular weight). In some embodiments, the number average molecular weight of A is between about 100 and about 10000, between about 200 and about 10000, between about 500 and about 10000, between about 1000 and about 10000, between about 2000 and about 10000, or between about 5000 and between about 10000. In some embodiments, the number average molecular weight of A is at least about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of A is less than about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of A is about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of A is between about 200 and about 10000.

In some embodiments, the number average molecular weight of B is between about 100 and about 20000, between about 200 and about 20000, between about 500 and about 20000, between about 1000 and about 20000, between about 2000 and about 20000, or between about 5000 and between about 20000. In some embodiments, the number average molecular weight of B is at least about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of B is less than about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of B is about 100, about 200, about 300, about 400, about 500, about 600, about 700, about 800, about 900, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000, or about 20000. In some embodiments, the number average molecular weight of B is between about 1000 and about 20000.

In some embodiments, the number average molecular weight of C is between about 100 and about 20000, between about 200 and about 20000, between about 500 and about 20000, between about 1000 and about 20000, between about 2000 and about 20000, or between about 5000 and between about 20000. In some embodiments, the number average molecular weight of C is at least about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of C is less than about 100, about 200, about 300, about 400, about 500, about 600, about 700, about 800, about 900, about 1000, about 2000, about 3000, about 4000, about 5000, about 6000, about 7000, about 8000, about 9000, about 10000, about 15000, or about 20000. In some embodiments, the number average molecular weight of C is about 100, about 200, about 300, about 400, about 500, about 600, about 700, about 800, about 900, about 1000, about 2000, about 3000, about 4000, about 5000, about 6000, about 7000, about 8000, about 9000, about 10000, about 11000, about 12000, about 13000, about 14000, about 15000, about 16000, about 17000, about 18000, about 19000, or about 20000. In some embodiments, the number average molecular weight of C is between about 1000 and about 20000.

In some embodiments according to any of the embodiments above, the biocompatible membrane comprises: between about 1 and about 10 parts by weight of A, between about 1 and about 5 parts by weight of B, between about 1 and about 5 parts by weight of C, and between about 1 and about 3 parts by weight of b.

In some embodiments according to any of the embodiments above, the linkage between each of A-b, B-b, and C-b is independently a urea linkage or a carbamate linkage. In some embodiments, the linkage between A-b is a urea linkage. In some embodiment, the linkage between A-b is a carbamate linkage. In some embodiment, the linkage between B-b is a urea linkage. In some embodiment, the linkage between B-b is a carbamate linkage. In some embodiment, the linkage between C-b is a urea linkage. In some embodiment, the linkage between C-b is a carbamate linkage.

In some embodiments according to any of the embodiments above, the biosensor further comprises an adhesive layer positioned between the detection layer and the biocompatible membrane, wherein the adhesive layer comprises a polymer comprising a first monomer comprising at least two amine moieties crosslinked with a second monomer comprising at least two formyl moieties.

In some embodiments, the first monomer comprises at least two, three, four, or five amine moieties. In some embodiments, the first monomer comprises two amine moieties. In some embodiments, the first monomer has the structure $H_2N$-alkylene-$NH_2$. "Alkylene" refers to divalent aliphatic hydrocarbyl groups preferably having from 1 to 8 carbon atoms that are either straight-chained or branched. Examples of alkylene include, but are not limited to, methylene (—$CH_2$—), ethylene (—$CH_2CH_2$—), n-propylene (—CH$_2$CH$_2$CH$_2$—), iso-propylene (—CH$_2$CH(CH$_3$)—), —C(CH$_3$)$_2$CH$_2$CH$_2$—, —C(CH$_3$)$_2$CH$_2$— and the like. In some embodiments, the first monomer is 1,6-diaminohexane.

In some embodiments, the second monomer comprises at least two, three, four, or five formyl moieties. In some embodiments, the second monomer comprises two formyl moieties. In some embodiments, the second monomer is glyoxal, malondialdehyde, succindialdehyde, glutaraldehyde, or phthalaldehyde. In some embodiments, the second monomer is glutaraldehyde.

In some embodiments according to any of the embodiments above, the biosensor further comprises a blank electrode which is substantially same as the working electrode, a counter electrode, and a reference electrode, wherein the blank electrode is directly covered by the biocompatible membrane or directly covered by the adhesive layer, which is covered by the biocompatible membrane. In some embodiments, the working and blank electrodes are comprised of substantially identical material(s), i.e., identical or nearly identical materials are used in both working and blank electrodes, and of substantially same size so that both electrodes have identical or nearly identical electron transfer properties. In some embodiments, the difference of the electron transfer properties between the two electrodes is less than 10%, 9%, 8%, 7%, 6%, 5%, 4%, 3%, 2%, 1%, or 0.5%. In some embodiments, the working and blank electrodes are made of identical material(s) and there is no difference in their electron transfer properties. In some embodiments, the working and counter electrodes are comprised of substantially identical material(s), i.e., identical or nearly identical materials are used in both working and counter electrodes so that both electrodes have identical or nearly identical electron transfer properties. In some embodiments, the difference of the electron transfer properties between the two electrodes is less than 10%, 9%, 8%, 7%, 6%, 5%, 4%, 3%, 2%, 1%, or 0.5%. In some embodiments, the working and counter electrodes are made of identical material(s) and there is no difference in their electron transfer properties.

In some embodiments, the minimum distance between the working electrode and the blank electrode is no more than about 1 mm, about 2 mm, about 3 mm, about 4 mm, about 5 mm, about 6 mm, about 7 mm, about 8 mm, about 9 mm, or about 10 mm. In some embodiments, the minimum distance between the working electrode and the blank electrode is less than about 1 mm, about 2 mm, about 3 mm, about 4 mm, about 5 mm, about 6 mm, about 7 mm, about 8 mm, about 9 mm, or about 10 mm. In some embodiments, the minimum distance between the working electrode and the blank electrode is about 1 mm, about 2 mm, about 3 mm, about 4 mm, about 5 mm, about 6 mm, about 7 mm, about 8 mm, about 9 mm, or about 10 mm. In some embodiments, the minimum distance between the working electrode and the blank electrode is no more than about 5 mm.

In some embodiments, the DC power supply comprises: a first circuit configured to apply a DC voltage to the working electrode, thereby generating a direct current on the working electrode; and a second circuit configured to apply a DC voltage to the blank electrode, thereby generating a direct current on the blank electrode, wherein the first circuit and second circuit are connected in parallel and the DC voltage applied to the working electrode and the DC voltage applied to the blank electrode are same relative to the reference electrode.

In some embodiments, the current measuring unit comprises: a first current measuring device configured to measure the direct current on the working electrode and communicate data regarding the direct current on the working electrode to the data processing unit, and a second current measuring device configured to measure the direct current on the working electrode and communicate data regarding the direct current on the blank electrode to the data processing unit.

In some embodiments, the AC impedance measuring unit is configured to apply a voltage comprising a DC component and an AC component to the working electrode and blank electrode, to measure a resulting current on the working electrode and a resulting current on the blank electrode, to determine an AC impedance of the working electrode and an AC impedance of the blank electrode, and to communicate data regarding the resulting currents and the AC impedances to the data processing unit. In some embodiments, the AC component has a frequency of between about 1 and about 1000, between about 1 and about 500, between about 1 and about 200, between about 1 and about 100, between about 1 and about 50, between about 1 and about 20, between about 20 and about 1000, between about 20 and about 500, between about 20 and about 200, between about 20 and about 100, between about 20 and about 50, between about 50 and about 1000, between about 50 and about 500, between about 50 and about 200, between about 50 and about 100, between about 100 and about 1000, between about 100 and about 500, or between about 100 and about 200 kHz. In some embodiments, the AC component has a frequency of between about 1 and about 100 kHz. In some embodiments, the AC component has a frequency of about 1 kHz. In some embodiments, the outputs of the AC impedance measuring unit may include the magnitude, phase, real part, and/or imaginary part of the measured AC impedance.

In some embodiments, the circuit switch controls the connection of the working electrode/blank electrode between the current measuring unit/AC impedance measuring unit. In some embodiments, the timing and/or frequency of the switching are determined by the control unit.

In some embodiments, the control unit controls the timing of the system, the timing and frequency of the operation of the current measuring unit, the timing and frequency of the AC impedance measuring unit, the status of the circuit switch, and/or the timing of the data transfer/analysis. In some embodiments, the operation frequency of the current measuring unit is at least about 100, about 50, about 20, about 10, about 9, about 8, about 7, about 6, about 5, about 4, about 3, or about 2 times of the operation frequency of the AC impedance measuring unit. In some embodiments, the operation frequency of the current measuring unit is at least about 10 times of the operation frequency of the AC impedance measuring unit.

In some embodiments, the data processing unit analyzes the outputs/data from the current measuring unit and the AC impedance measuring unit, determines the concentration of an analyte, and sends an output of the concentration to a receiving end.

Figure 3:
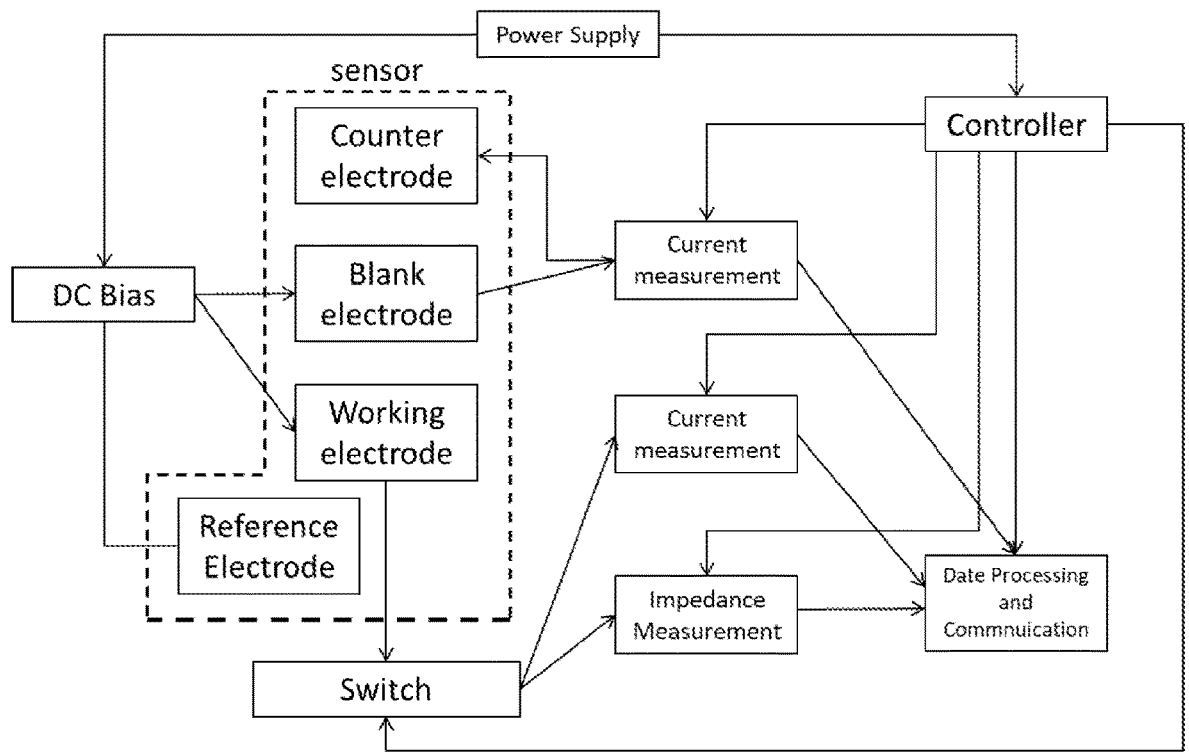
FIG. 3 shows an exemplary arrangement of the biosensing system.
Figure 4:
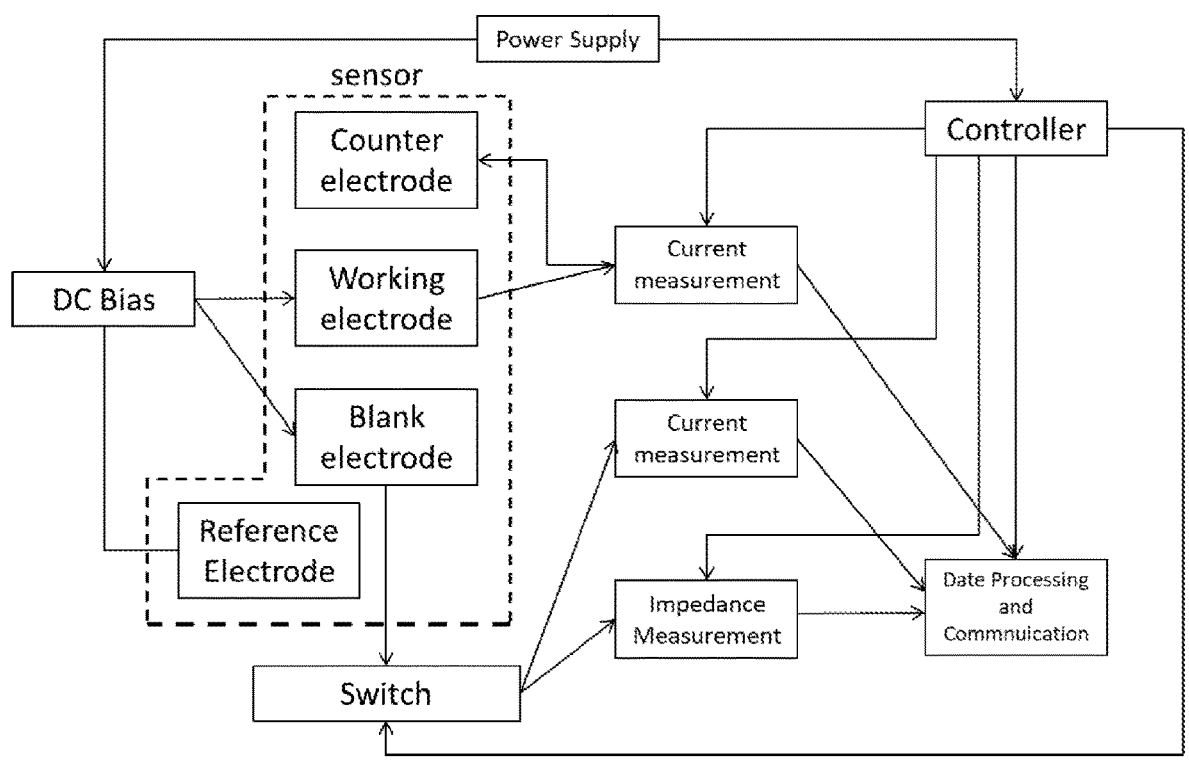
FIG. 4 shows another exemplary arrangement of the biosensing system.

In some embodiments, the components of the system are connected to each other as illustrated in FIG. 3 or FIG. 4.

Methods of Use

In another aspect, provided is a method of using the biosensing systems described herein to determine the concentration of an analyte in a sample. In some embodiments, the method comprises Step A, which comprises determining whether the operation time T=t1−t0 exceeds a predetermined value Tmax. In some embodiments, in response to the determination that T exceeds Tmax, a warning is returned. In some embodiments, in response to the determination that T does not exceed Tmax, Step B is conducted.

In some embodiments, the method comprises Step B, which comprises determining whether the operation time T exceeds a predetermined initiation time. In some embodiments, in response to the determination that T exceeds the predetermined initiation time, Step C is conducted. In some embodiments, in response to the determination that T does not exceed the predetermined initiation time, Step A is repeated.

In some embodiments, the method comprises Step C, which comprises: (1) applying a DC voltage to the working electrode and the blank electrode, thereby generating a direct current on the working electrode and a direct current on the blank electrode; (2) measuring the direct current on the working electrode and the direct current on the blank electrode; (3) measuring an AC impedance of the working electrode and/or an AC impedance of the blank electrode; and (4) determining concentration of the analyte based on the measured direct currents and AC impedances.

In some embodiments, step (1) comprises: (a) applying a DC voltage to the working electrode, thereby generating a direct current on the working electrode; and (b) applying a DC voltage to the blank electrode, thereby generating a direct current on the blank electrode, wherein the DC voltage applied to the working electrode and the DC voltage applied to the blank electrode are same relative to the reference electrode.

In some embodiments, step (3) comprises: (a) applying a voltage comprising a DC component and an AC component to the working electrode and blank electrode; (b) measuring a resulting current on the working electrode and a resulting current on the blank electrode; and (c) determining an AC impedance of the working electrode and an AC impedance of the blank electrode.

In some embodiments, step (4) comprises: (a) reading a direct current (I1) on the working electrode, the time (t1) when I1 is measured, a direct current (I2) on the blank electrode, the time (t2) when I2 is measured, wherein t2 is within ±30 seconds from t1. In some embodiments, I1 and I2 are processed via suitable signal processing methods such as noise filtering. In some embodiments, the I1 and I2 used in the steps described below are values after noise filtering.

In some embodiments, step (4) comprises: (b) determining an analyte current (I) and a time (t) using the following formulae:

$$I=I1-I2, \text{ and} \quad (i)$$

$$t=(t1\pm t2)/2; \quad (ii)$$

In some embodiments, step (4) comprises: (c) determining concentration of the analyte (C1) using the formula C1=f(I, X), wherein X is a conversion factor determined using the following steps:
(i) determining if the biosensor has been calibrated,
in response to the determination that the biosensor has not been calibrated, setting X' as a predetermined value X0 and setting the calibration time as 0, and
in response to the determination that biosensor has been calibrated, determining X' using the formula X'=f$^{-1}$(I(tc0), C0) and setting tc' as tc0, wherein f$^{-1}$(I(tc0), C0) is inverse operation of f(I, X), C0 is the concentration of the analyte in the calibration, tc0 is the time when the calibration is conducted, I(tc0) is an analyte current measured at a time closest to the latest calibration, wherein I(tc0) is measured within 5 minutes before or after the latest calibration, (ii) determining if the latest calibration time is after the latest measurement of impedance,
in response to the determination that the latest calibration time is after the latest impedance measurement, setting X as X' and finishing the determination of X,
in response to the determination that the latest calibration time is not after the latest impedance measurement, reading the real part of the latest impedance (Zre_cal) and the imaginary part of the latest impedance (Zim_cal) and proceeding to step (iii),
(iii) determining if the real part of the currently measured impedance (Zre) is within a first predetermined range and if the imaginary part of the currently measured impedance (Zim) is within a second predetermined range,
in response to the determination that Zre is not within the first predetermined range or Zim is not within the second predetermined range, sending an error message and finishing the determination of X,
in response to the determination that Zre is within the first predetermined range and Zim is within the second predetermined range, proceeding to step (iv),
(iv) determining the real part difference (dZre) and the imaginary part difference (dZim) using the following formulae:

$$dZre=Zre-Zre\_cal, \text{ and}$$

$$dZim=Zim-Zim\_cal,$$

(v) determining if absolute value of dZre is larger than a predetermined threshold dZre_thres and if absolute value of dZim is larger than a predetermined threshold dZim_thres,
in response to the determination that absolute value of dZre is not larger than dZre_thres and absolute value of dZim is not larger than dZim_thres, setting X as X' and finishing the determination of X,
in response to the determination that absolute value of dZre is larger than dZre_thres or absolute value of dZim is larger than dZim_thres, proceeding to steps (vi)-(x),
(vi) in response to the determination that dZre>0, dZre>dZre_thres, dZim>0, and dZim>dZim_thres, setting X=X'*h(Zre/Zre_cal, Zim/Zim_cal), wherein h(Zre/Zre_cal, Zim/Zim_cal)>1,
(vii) in response to the determination that dZre>0, dZre>dZre_thres, and dZim≤ dZim_thres, setting X=X'*j(Zre/Zre_cal), wherein j(Zre/Zre_cal)>1,
(viii) in response to the determination that dZre<0 and dZre←dZre_thres, setting X=X'*k(Zre/Zre_cal), wherein k(Zre/Zre_cal)<1,
(ix) in response to the determination that −dZre_thres<dZre<dZre_thres, dZim>0, and dZim>dZim_thres, setting X=X'*m(Zim/Zim_cal), wherein m(Zim/Zim_cal)>1,
(x) in response to the determination that −dZre_thres<dZre<dZre_thres, dZim<0, and dZim←dZim_thres, setting X=X'*n(Zim/Zim_cal), wherein n(Zim/Zim_cal)<1.

Figure 5:
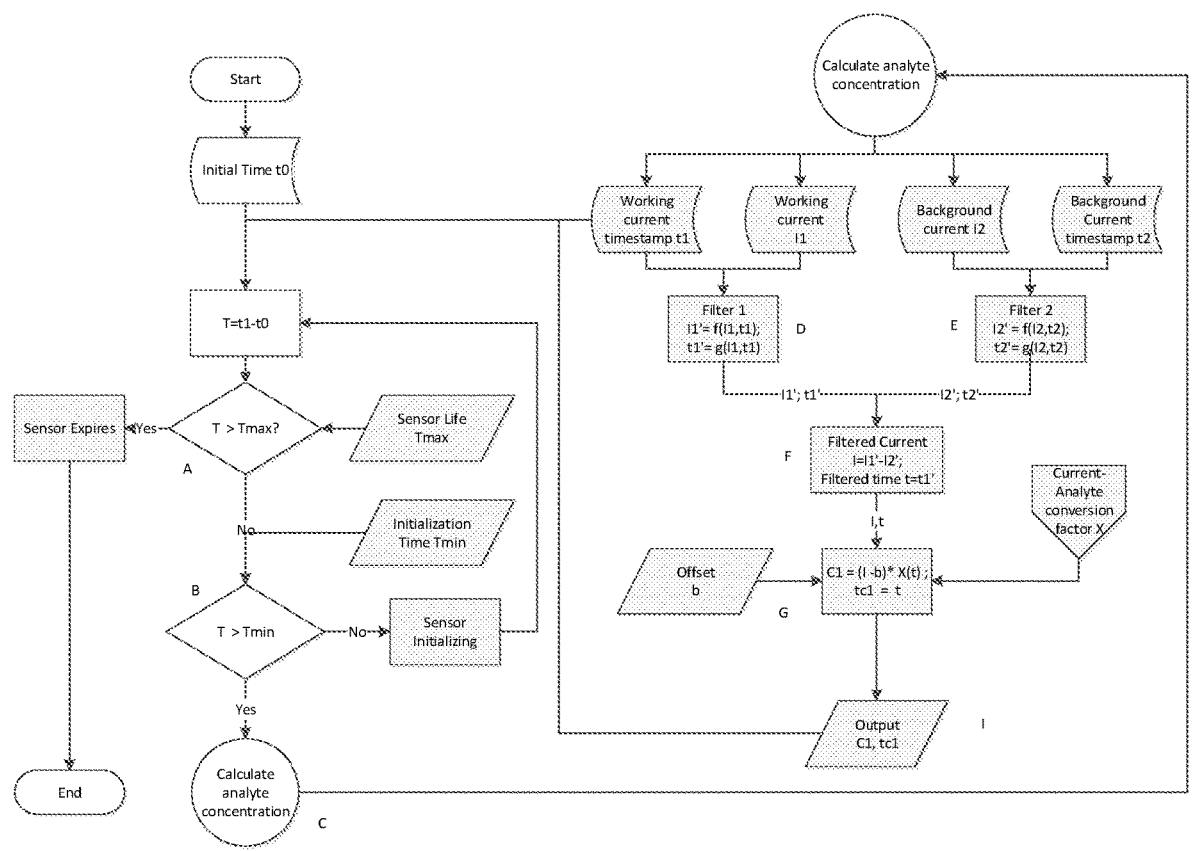
FIG. 5 shows an exemplary algorithm of using the biosensing system to determine the concentration of an analyte.
Figure 6:
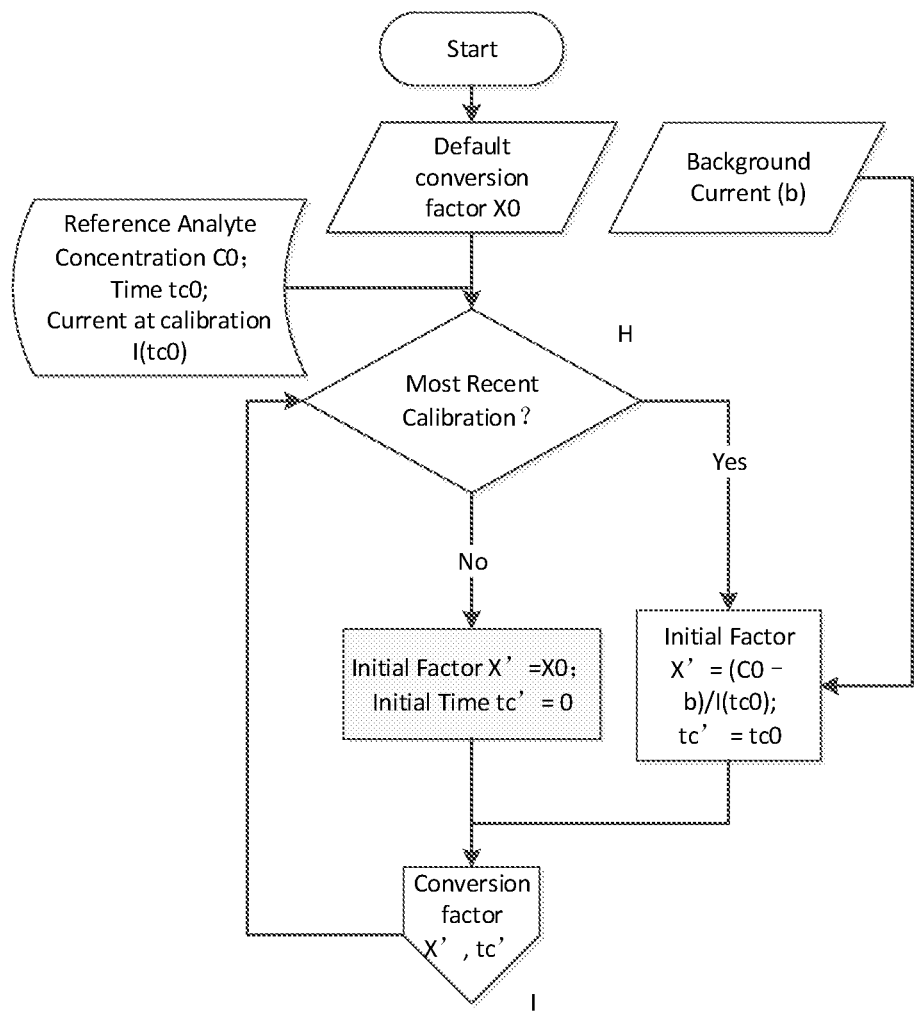
FIG. 6 shows an exemplary algorithm of calculating conversion factor X'.
Figure 7:
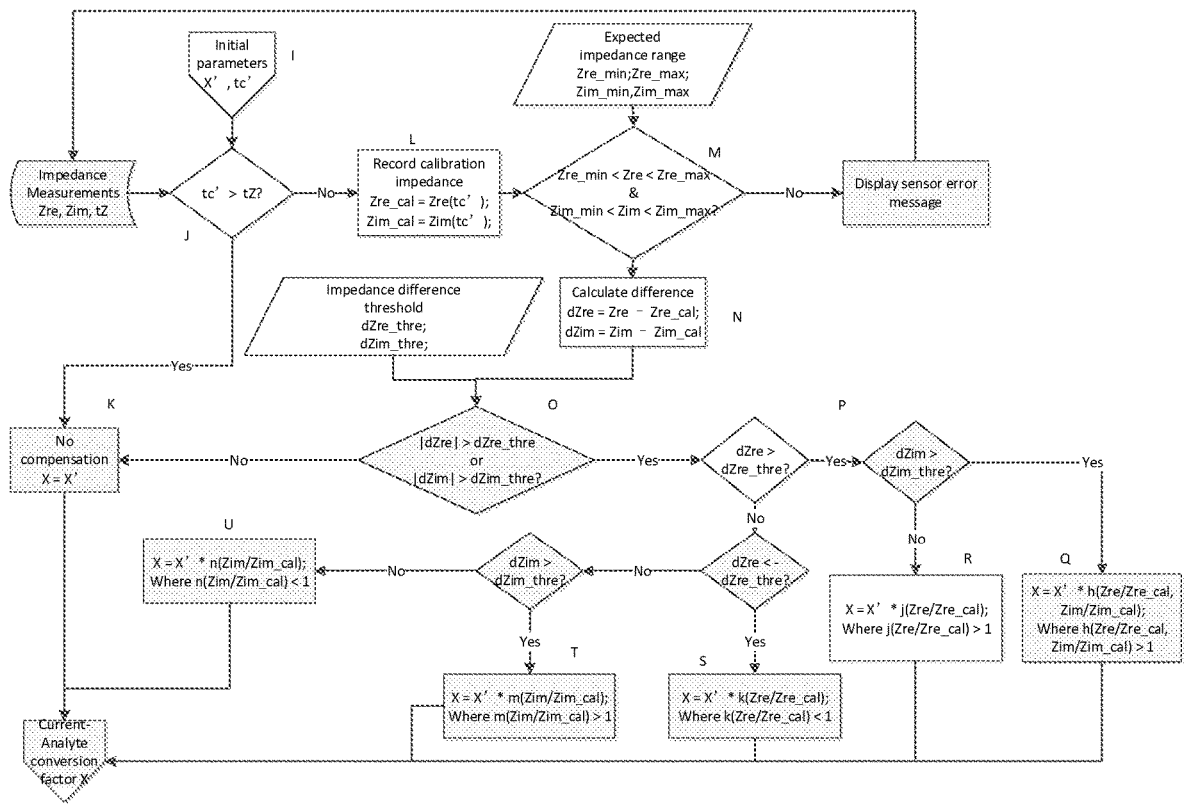
FIG. 7 shows an exemplary algorithm of calculating conversion factor X.

Exemplary algorithms for the methods described herein are shown in FIG. 5, FIG. 6, and FIG. 7.

In some embodiments, f(I, X)=(I−b)*X, wherein b is a pre-determined background current value. In some embodiments, f$^{-1}$(I(tc0), C0)=C0/(I(tc0)−b).

In some embodiments, the function h(Zre/Zre_cal, Zim/Zim_cal) is any suitable function that generates a result that is more than 1. In some embodiments, h(Zre/Zre_cal, Zim/Zim_cal)=Zre/Zre_cal+Zim/Zim_cal−1.

In some embodiments, the function j(Zre/Zre_cal) is any suitable function that generates a result that is more than 1. In some embodiments, j(Zre/Zre_cal)=Zre/Zre_cal.

In some embodiments, the function k(Zre/Zre_cal) is any suitable function that generates a result that is less than 1. In some embodiments, k(Zre/Zre_cal)=Zre/Zre_cal.

In some embodiments, the function m(Zim/Zim_cal) is any suitable function that generates a result that is more than 1. In some embodiments, m(Zim/Zim_cal)=Zim/Zim_cal.

In some embodiments, the function n(Zim/Zim_cal) is any suitable function that generates a result that is less than 1. In some embodiments, n(Zim/Zim_cal)=Zim/Zim_cal.

In some embodiments, the method further comprises a step of determining the condition of the biosensor, wherein the step is conducted within 5 minutes after the biosensor is coupled to the DC power supply, current measuring unit, AC impedance measuring unit, circuit switch control unit, and data processing unit and comprises:
  (a) measuring an AC impedance of the working electrode;
  (b) determining if the real part of the measured impedance (Zre) is within a first predetermined range and if the imaginary part of the currently measured impedance (Zim) is within a second predetermined range,
    in response to the determination that Zre is not within the first predetermined range or Zim is not within the second predetermined range, starting an initialization sequence to prepare the biosensor,
    in response to the determination that Zre is within the first predetermined range and Zim is within the second predetermined range, proceeding to step (1).

EXAMPLES

The following examples are offered to illustrate but not to limit the biosensors and methods of preparation thereof disclosed herein.

Example 1. Formation of Detection Layer on Electrode

An exemplary method of forming the detection layer on the electrode is illustrated in FIG. 1 and detailed below.

Step 1—A platinum electrode was formed on a glass substrate via etching.

Step 2—Peptide probe molecule (glucose oxidase), dopamine, and chloroplatinic acid were added to water at 30° C. The concentrations of glucose oxidase, dopamine, and chloroplatinic acid were 5 mg/mL, 5 g/L, and 5 mg/L, respectively. The pH of the solution was adjusted to 8 and the dissolved oxygen concentration saturation in the solution was less than 1%. Metallic nanoparticles with a coating containing polydopamine and the peptide probe were thereby formed in the solution.

Step 3—The platinum electrode prepared in step 1 was placed into the solution of step 2 and the metallic nanoparticles formed in step 2 were deposited on top of the electrode via an electrochemical oxidation reaction. The potential applied to the electrode relative to a silver/silver chloride reference solution electrode was 0.4 V.

Example 2. Formation of Detection Layer on Electrode

Figure 2:
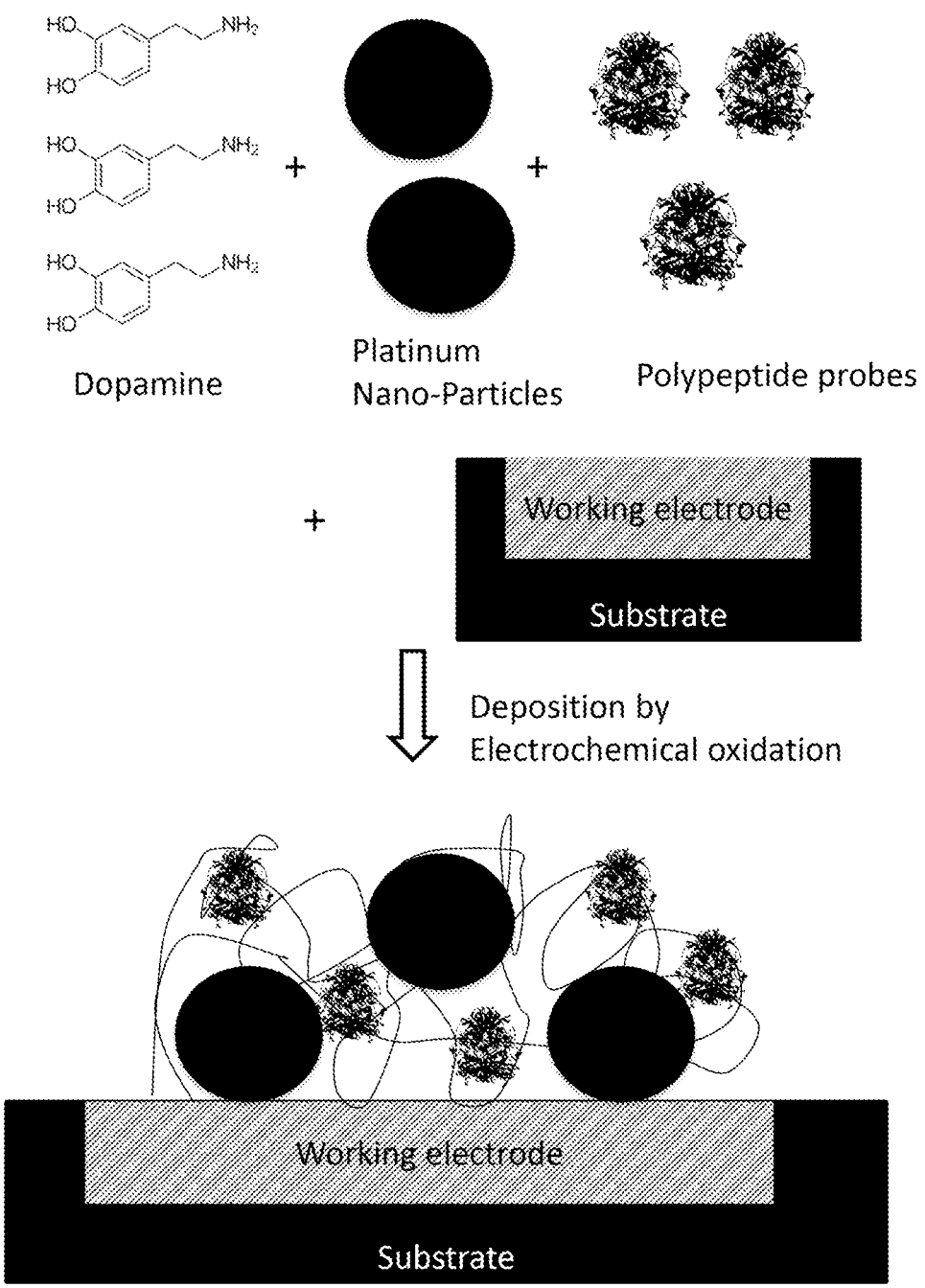
FIG. 2 shows another exemplary process of forming the detection layer on top of the working electrode.

Another exemplary method of forming the detection layer on top of the electrode is illustrated in FIG. 2 and detailed below.

Step 1—A gold electrode was formed on a polydimethylsiloxane substrate via screen printing.

Step 2—Gold nanoparticle, peptide probe molecule (hepatitis B antibody), and dopamine were added to water at 35° C. The size of the gold nanoparticle was about 50 nanometers. The concentrations of the gold nanoparticle, peptide probe molecule, and dopamine were 25000 ppm, 4 mg/mL, and 6 g/L, respectively. The pH of the solution was adjusted to 7 and the dissolved oxygen concentration saturation in the solution was less than 1%. The gold electrode prepared in step 1 was immersed in the solution. A detection layer containing polydopamine, gold nanoparticle, and peptide probe was formed on top of the electrode via an electrochemical oxidation reaction. The potential applied to the electrode relative to a silver/silver chloride reference solution electrode was 0.6 V.

Example 3. Formation of Biocompatible Membrane i. Example 3.1

Step 1—Polyetheramine (number average molecular weight: 1000; 25 g), polycarbonate diol (number average molecular weight: 5000; 10 g), diamino-terminated polydimethylsiloxane (number average molecular weight: 5000; 15 g) were added to 100 mL of tetrahydrofuran at 40° C. and mixed well.

Step 2—To the solution of step 1 was added triethylenediamine. 12 g methylene diphenyl diisocyanate was then added dropwise. The mixture was reacted at 65° C. for 12 h.

Step 3—To the solution of step 2 was added 50 mL deionized water and the mixture was reacted for 12 h.

The resulting triblock polymer was applied to the detection layer formed in Example 1 or 2 using suitable methods.

ii. Example 3.2

Step 1—Amino-terminated polyethylene glycol (number average molecular weight: 2000; 20 g), polycarbonate diol (number average molecular weight: 2000; 15 g), poly(methyl methacrylate) (number average molecular weight: 2000; 15 g), and diamino-terminated polydimethylsiloxane (number average molecular weight: 8000; 15 g) were added to 500 mL of tetrahydrofuran at 30° C. and mixed well.

Step 2—To the solution of step 1 was added triethylenediamine. A mixture of methylene diphenyl diisocyanate and bis(4-isocyanatocyclohexyl)methane was then added dropwise. The mixture was reacted at 55° C. for 14 h.

Step 3—To the solution of step 2 was added 500 mL deionized water and the mixture was reacted for 18 h.

The resulting triblock polymer was applied to the detection layer formed in Example 1 or 2 using suitable methods.

iii. Example 3.3

Step 1—Amino-terminated polypropylene glycol (molecular weight: 500; 15 g), polyetheramine (molecular weight: 600; 10 g), poly(bisphenol A polycarbonate) (molecular weight: 5000; 25 g), diamino-terminated polydimethylsiloxane (molecular weight: 20000; 10 g), poly(2-hydroxyethyl methacrylate) (molecular weight: 5000; 5 g) were added to 150 mL isobutanol at 35° C. and mixed well.

Step 2—To the solution of step 1 was added dibutyltin bis(2-ethylhexanoate). 15 g hexamethylene diisocyanate was then added dropwise. The mixture was reacted at 60° C. for 16 h.

Step 3—To the solution of step 2 was added 150 mL deionized water and the mixture was reacted for 14 h.

The resulting triblock polymer was applied to the detection layer formed in Example 1 or 2 using suitable methods.

iv. Example 3.4

Step 1—Amino-terminated polyethylene glycol (number average molecular weight: 10000; 30 g), polycarbonate diol (number average molecular weight: 2000; 5 g), poly (methyl methacrylate) (number average molecular weight: 2000; 5 g), and poly(2-hydroxyethyl methacrylate) (molecular weight: 20000; 15 g) were added to 600 mL isobutanol at 35° C. and mixed well.

Step 2—To the solution of step 1 was added dibutyltin bis(2-ethylhexanoate). 20 g bis(4-isocyanatocyclohexyl) methane was then added dropwise. The mixture was reacted at 70° C. for 16 h.

The resulting triblock polymer was applied to the detection layer formed in Example 1 or 2 using suitable methods.

Example 4. Formation of Adhesive Layer

Step 1-10 g 1,6-diaminohexane was dissolved in 100 mL ethanol.

Step 2—The substrate with a detection layer formed in Example 1 or 2 was immersed in the solution of step 1 for 10 minutes, rinsed three times with ethanol, immersed in ethanol for 10 minutes, and dried.

Step 3—The substrate prepared in step 2 was exposed to glutaraldehyde in gas phase at 40° C. for 10 minutes.

Step 4—The solution formed in any one of Examples 3.1-3.4 was applied to the substrate prepared in step 3 and a biocompatible membrane was formed via spin coating.

Example 5

Figure 8:
FIG. 8 shows current outputs over time at different glucose concentrations for different biosensors.

A biosensor that only has the detection layer as described herein, a biosensor that only has the biocompatible membrane and detection probe layer deposited by conventional methods as described herein, and a biosensor that has the detection layer, the biocompatible membrane, and the adhesive layer as described herein were exposed to a glucose solution. For each biosensor, a constant potential was applied to the working electrode and the current output on the working electrode was measured at six glucose concentrations: 0 mmol/L, 5 mmol/L, 10 mmol/L, 15 mmol/L, 20 mmol/L, and 25 mmol/L. FIG. 8 shows the current output over time at different glucose concentrations for each biosensor. As shown in FIG. 8, the biosensor that has the detection layer, the biocompatible membrane, and the adhesive layer as described herein showed more stable current output over time and better linearity in response to increase in glucose concentration.

While the foregoing description of the biosensors and methods described herein enables one of ordinary skill to make and use the biosensors and methods described herein, those of ordinary skill will understand and appreciate the existence of variations, combinations, and equivalents of the specific embodiment, method, and examples herein. The biosensors and methods provided herein should therefore not be limited by the above-described embodiments, methods, or examples, but rather encompasses all embodiments and methods within the scope and spirit of the compounds, uses, and methods provided herein.

It will be appreciated that, for clarity purposes, the above description has described examples of the invention with reference to different functional units and modules. However, it will be apparent that any suitable distribution of functionality between different functional units, processing logic elements or domains may be used without detracting from the invention. For example, functionality illustrated to be performed by separate processing logic elements, or controllers, may be performed by the same processing logic element, or controller. Hence, references to specific functional units are only to be seen as references to suitable means for providing the described functionality, rather than indicative of a strict logical or physical structure or organization.

In the foregoing description of examples, reference is made to the accompanying drawings which form a part hereof, and in which it is shown by way of illustration specific examples in which the invention may be practiced. It is to be understood that other examples may be utilized and structural changes may be made without departing from the scope of the claimed subject matter.

It should be understood that the specific order or hierarchy of steps in the processes disclosed herein is an example of exemplary approaches. Based upon design preferences, it is understood that the specific order or hierarchy of steps in the processes may be rearranged while remaining within the scope of the claimed subject matter.

What is claimed is:

1. A biosensing system, comprising:
   (1) a biosensor, comprising:
      a substrate,
      a working electrode on top of the substrate,
      a detection layer on top of the working electrode,
      a biocompatible membrane on top of the detection layer,
      a blank electrode, wherein the blank electrode is substantially same as the working electrode and covered directly by the biocompatible membrane,
      a reference electrode, and
      a counter electrode;
   (2) a DC power supply;
   (3) a current measuring unit;
   (4) an AC impedance measuring unit;
   (5) a circuit switch;
   (6) a control unit; and
   (7) a data processing unit, wherein the biosensor further comprises an adhesive layer between the detection layer and the biocompatible membrane on top of the working electrode and between the biocompatible membrane and the blank electrode, and wherein the adhesive layer comprises a polymer comprising a first monomer comprising at least two amine moieties cross-linked with a second monomer comprising at least two formyl moieties.

2. The biosensing system of claim 1, wherein the working electrode comprises carbon, graphene, gold, or platinum.

3. The biosensing system of claim 1, wherein the detection layer comprises a metallic nanoparticle, polydopamine, and a peptide probe.

4. The biosensing system of claim 3, wherein the metallic nanoparticle is a platinum nanoparticle, a gold nanoparticle, or an iridium nanoparticle.

5. The biosensing system of claim 3, wherein the metallic nanoparticle has a dimension of between 1 and 100 nanometers.

6. The biosensing system of claim 3, wherein the peptide probe comprises an enzyme, an antibody, or a polymer comprising a peptide.

7. The biosensing system of claim 3, wherein the peptide probe comprises an oxidoreductase.

8. The biosensing system of claim 3, wherein the peptide probe comprises glucose oxidase, glucose dehydrogenase, or horseradish peroxidase.

9. The biosensing system of claim 3, wherein the metallic nanoparticle is coated with polydopamine and the peptide probe.

10. The biosensing system of claim 3, wherein the metallic nanoparticle is admixed with polydopamine and the peptide probe.

11. The biosensing system of claim 1, wherein the biocompatible membrane comprises a triblock polymer A-b-B-b-C, wherein:
   A is a hydrophilic soft segment,
   B is a hydrophobic hard segment,
   C is a flexible polymer segment, and
   b is a chain extender.

12. The biosensing system of claim 11, wherein the hydrophilic soft segment comprises a polymer selected from the group consisting of polyethylene glycol (PEG), polypropylene glycol (PPG), and polyetheramine (PEA).

13. The biosensing system of claim 11, wherein the hydrophobic hard segment comprises a polymer selected from the group consisting of polycarbonate (PC) and poly(methyl methacrylate) (PMMA).

14. The biosensing system of claim 11, wherein the flexible polymer segment comprises a polymer selected from the group consisting of polydimethylsiloxane (PDMS) and poly(2-hydroxyethyl methacrylate) (PHEMA).

15. The biosensing system of claim 11, wherein the chain extender in the biocompatible membrane is derived from a compound comprising an isocyanate.

16. The biosensing system of claim 11, wherein each chain extender is independently derived from methylene diphenyl diisocyanate (MDI), hexamethylene diisocyanate (HDI), or bis(4-isocyanatocyclohexyl)methane.

17. The biosensing system of claim 11, wherein:
   a number average molecular weight of A is between 200 and 10000,
   a number average molecular weight of B is between 1000 and 20000, and
   a number average molecular weight of C is between 1000 and 20000.

18. The biosensing system of claim 11, wherein the biocompatible membrane comprises:
   between 1 and 10 parts by weight of A,
   between 1 and 5 parts by weight of B,
   between 1 and 5 parts by weight of C, and
   between 1 and 3 parts by weight of b.

19. The biosensing system of claim 11, wherein the linkage between each of A-b, B-b, and C-b is independently a urea linkage or a carbamate linkage.

20. The biosensing system of claim 1, wherein the first monomer is 1,6-diaminohexane and the second monomer is glutaraldehyde.

21. The biosensing system of claim 1, wherein a minimum distance between the working electrode and the blank electrode is no more than 5 mm.

22. The biosensing system of claim 1, wherein the DC power supply comprises:
   a first circuit configured to apply a DC voltage to the working electrode, thereby generating a direct current on the working electrode; and
   a second circuit configured to apply a DC voltage to the blank electrode, thereby generating a direct current on the blank electrode,
   wherein the first circuit and second circuit are connected in parallel and the DC voltage applied to the working electrode and the DC voltage applied to the blank electrode are same relative to the reference electrode.

23. The biosensing system of claim 1, wherein the current measuring unit comprises:
   a first current measuring device configured to measure the direct current on the working electrode and communicate data regarding the direct current on the working electrode to the data processing unit, and
   a second current measuring device configured to measure the direct current on the working electrode and communicate data regarding the direct current on the blank electrode to the data processing unit.

24. The biosensing system of claim 1, wherein the AC impedance measuring unit is configured to apply a voltage comprising a DC component and an AC component to the working electrode and blank electrode, to measure a resulting current on the working electrode and a resulting current on the blank electrode, to determine an AC impedance of the working electrode and an AC impedance of the blank electrode, and to communicate data regarding the resulting currents and the AC impedances to the data processing unit.

25. The biosensing system of claim 24, wherein the AC component has a frequency of 1-100 kHz.

26. The biosensing system of claim 1, wherein the data from the AC impedance measuring unit comprises the magnitude, phase, real part, and/or imaginary part of the measured AC impedance.

27. The biosensing system of claim 1, wherein the operation frequency of the current measuring unit is at least about 10 times of the operation frequency of the AC impedance measuring unit.

28. A method of using the biosensing system of claim 1 to detect the concentration of an analyte in a sample, comprising:
   (1) applying a DC voltage to the working electrode and the blank electrode, thereby generating a direct current on the working electrode and a direct current on the blank electrode;
   (2) measuring the direct current on the working electrode and the direct current on the blank electrode;
   (3) measuring an AC impedance of the working electrode and/or an AC impedance of the blank electrode; and
   (4) determining concentration of the analyte based on the measured direct currents and AC impedances.

29. The method of claim 28, wherein step (1) comprises:
   (a) applying a DC voltage to the working electrode, thereby generating a direct current on the working electrode; and
   (b) applying a DC voltage to the blank electrode, thereby generating a direct current on the blank electrode,
   wherein the DC voltage applied to the working electrode and the DC voltage applied to the blank electrode are same relative to the reference electrode.

30. The method of claim 28, wherein step (3) comprises:
   (a) applying a voltage comprising a DC component and an AC component to the working electrode and blank electrode;
   (b) measuring a resulting current on the working electrode and a resulting current on the blank electrode; and
   (c) determining an AC impedance of the working electrode and an AC impedance of the blank electrode.

31. The method of claim 28, wherein step (4) comprises:
   (a) reading a direct current (I1) on the working electrode, the time (t1) when I1 is measured, a direct current (I2)

on the blank electrode, the time (t2) when I2 is measured, wherein t2 is within ±30 seconds from t1;

(b) determining an analyte current (I) and a time (t) using the following formulae:

$$I = I1 - I2, \text{ and} \quad (i)$$

$$t = (t1 \pm t2)/2; \quad (ii)$$

(c) determining concentration of the analyte (C1) using the formula C1=f(I, X), wherein f(I, X)=(I-b)*X, b is a pre-determined background current value, and X is a conversion factor determined using the following steps:
  (i) determining if the biosensor has been calibrated,
    in response to the determination that the biosensor has not been calibrated, setting X' as a predetermined value X0 and setting the calibration time as 0, and
    in response to the determination that biosensor has been calibrated, determining X' using the formula X'=$f^{-1}$(I(tc0), C0) and setting tc' as tc0, wherein $f^{-1}$(I(tc0), C0) is inverse operation of f(I, X), C0 is the concentration of the analyte in the calibration, tc0 is the time when the calibration is conducted, I(tc0) is an analyte current measured at a time closest to the latest calibration, wherein I(tc0) is measured within 5 minutes before or after the latest calibration,
  (ii) determining if the latest calibration time is after the latest measurement of impedance,
    in response to the determination that the latest calibration time is after the latest impedance measurement, setting X as X' and finishing the determination of X,
    in response to the determination that the latest calibration time is not after the latest impedance measurement, reading the real part of the latest impedance (Zre_cal) and the imaginary part of the latest impedance (Zim_cal) and proceeding to step (iii),
  (iii) determining if the real part of the currently measured impedance (Zre) is within a first predetermined range and if the imaginary part of the currently measured impedance (Zim) is within a second predetermined range,
    in response to the determination that Zre is not within the first predetermined range or Zim is not within the second predetermined range, sending an error message and finishing the determination of X,
    in response to the determination that Zre is within the first predetermined range and Zim is within the second predetermined range, proceeding to step (iv),
  (iv) determining the real part difference (dZre) and the imaginary part difference (dZim) using the following formulae:

$$dZre = Zre - Zre\_cal, \text{ and}$$

$$dZim = Zim - Zim\_cal,$$

(v) determining if absolute value of dZre is larger than a predetermined threshold dZre_thres and if absolute value of dZim is larger than a predetermined threshold dZim_thres,
    in response to the determination that absolute value of dZre is not larger than dZre_thres and absolute value of dZim is not larger than dZim_thres, setting X as X' and finishing the determination of X,
    in response to the determination that absolute value of dZre is larger than dZre_thres or absolute value of dZim is larger than dZim_thres, proceeding to steps (vi)-(x),
  (vi) in response to the determination that dZre>0, dZre>dZre_thres, dZim>0, and dZim>dZim_thres, setting X=X'*h(Zre/Zre_cal, Zim/Zim_cal), wherein h(Zre/Zre_cal, Zim/Zim_cal)>1,
  (vii) in response to the determination that dZre>0, dZre>dZre_thres, and dZim≤dZim_thres, setting X=X'*j(Zre/Zre_cal), wherein j(Zre/Zre_cal)>1,
  (viii) in response to the determination that dZre<0 and dZre<−dZre_thres, setting X=X'*k(Zre/Zre_cal), wherein k(Zre/Zre_cal)<1,
  (ix) in response to the determination that −dZre_thres<dZre<dZre_thres, dZim>0, and dZim>dZim_thres, setting X=X'*m(Zim/Zim_cal), wherein m(Zim/Zim_cal)>1,
  (x) in response to the determination that −dZre_thres<dZre<dZre_thres, dZim<0, and dZim<−dZim_thres, setting X=X'*n(Zim/Zim_cal), wherein n(Zim/Zim_cal)<1.

32. The method of claim 28, further comprising a step of determining the condition of the biosensor, wherein the step is conducted within 5 minutes after the biosensor is coupled to the DC power supply, current measuring unit, AC impedance measuring unit, circuit switch control unit, and data processing unit and comprises:
  (a) measuring an AC impedance of the working electrode;
  (b) determining if the real part of the measured impedance (Zre) is within a first predetermined range and if the imaginary part of the currently measured impedance (Zim) is within a second predetermined range,
    in response to the determination that Zre is not within the first predetermined range or Zim is not within the second predetermined range, starting an initialization sequence to prepare the biosensor,
    in response to the determination that Zre is within the first predetermined range and Zim is within the second predetermined range, proceeding to step (1).

* * * * *